US007691968B2

(12) United States Patent
Evans et al.

(10) Patent No.: US 7,691,968 B2
(45) Date of Patent: Apr. 6, 2010

(54) PROCESS FOR THE SYNTHESIS OF PEPTIDES AMIDES BY SIDE-CHAIN ATTACHMENT TO A SOLID PHASE

(75) Inventors: David John Evans, Manchester (GB); Dean Steven Anthony Simpkin, Stirlingshire (GB); Donald Alfred Wellings, Manchester (GB); Eric Atherton, Northwich (GB)

(73) Assignee: Avecia Biologics Limited, Blackley (GB)

( * ) Notice: Subject to any disclaimer, the term of this patent is extended or adjusted under 35 U.S.C. 154(b) by 1257 days.

(21) Appl. No.: 10/513,285

(22) PCT Filed: May 2, 2003

(86) PCT No.: PCT/GB03/01949

§ 371 (c)(1),
(2), (4) Date: Jul. 26, 2005

(87) PCT Pub. No.: WO03/093302

PCT Pub. Date: Nov. 13, 2003

(65) Prior Publication Data

US 2005/0266520 A1 Dec. 1, 2005

(30) Foreign Application Priority Data

| May 3, 2002 | (GB) | ................................ | 0210183.0 |
| May 3, 2002 | (GB) | ................................ | 0210184.8 |
| May 3, 2002 | (GB) | ................................ | 0210185.5 |

(51) Int. Cl.
*A61K 38/00* (2006.01)
*A61K 8/64* (2006.01)

(52) U.S. Cl. ...................... 530/334; 530/335; 424/70.51
(58) Field of Classification Search ...................... None
See application file for complete search history.

(56) References Cited

U.S. PATENT DOCUMENTS

| 4,033,940 | A | | 7/1977 | Hughes et al. ............... 530/307 |
| 5,318,899 | A | * | 6/1994 | Scarborough et al. ...... 435/69.6 |
| 5,602,231 | A | | 2/1997 | Cotton et al. ............... 530/334 |
| 5,851,839 | A | | 12/1998 | Scarborough ............... 436/518 |
| 5,888,972 | A | | 3/1999 | Hemmi et al. ................ 514/18 |
| 6,008,058 | A | | 12/1999 | Spatola et al. .............. 436/518 |

FOREIGN PATENT DOCUMENTS

WO WO 90/15620 12/1990

WO WO 00/26262 5/2000

OTHER PUBLICATIONS

Liu, 2000, Bioorganic & Medicinal Chemistry Letters, 10, 1361-1363.*
Barlos, et al., 1991, Int. J. Peptide Res., 38, 555-561.*
Cabrele, et al., 1999, J. Org. Chem., 64, 4353-4361.*
Delaet, et al., 1995, Letters in Peptide Science, 2, 325-331.*
G Liu et al .: "Solid-Phase Synthesis of Muramyl Dipeptide (MDP) Derivatives Using a Multipin Method" Bioorganic & Medicinal Chemistry Letters, vol. 10, No. 19, 2000, pp. 1361-1363, XP004207005 Oxford, GB ISSN: 0960-894X.
Z Yao et al.: "Preparation of L-N-Alpha-FMOC-4- 'Di-(Tert-Butyl)-Phosphon Omethyl!!! Phenylalanine From L-Tyrosine" Tetrahedron: Asymmetry., vol. 10, 1999, pp. 3727-3734, XP002259356 Elsevier Science Publishers, Amsterdam., NL ISSN: 0957-4166.
Z Yao et al.: "Synthesis of FMOC-Protected 4-Carboxydifluoromethyl-L-Phenylalanine: A Phosphotyrosylmimetic of Potential Use for Signal Transduction Studies" Tetrahedron., vol. 55, 1999 pp. 2865-2874, XP004157124 Elsevier Science Publishers, Amsterdam ., NL ISSN: 0040-4020.
Bui, Chinh T. et al.: Solid Phase Synthesis of C-Terminal Peptide Amides, XP-002259357 & Journal of Peptide Science (2000), 6(5), 243-250, 2000 Abstract.
Delaet, N. G .J. et al.: Convenient Solid Phase Synthesis Method for Preparation of Cysteine C-Terminally Derivatized Peptides, XP002259358 & Letters in Peptide Science (1996), 2 (6), 325-31, 1996, Abstract.
Kominami, Goro et al.: "A Highly Specific and Sensitive Radioimmunoassay of Caerulein an Analog of Cholecystokinin-8" XP002259359 & Journal of Immunoassay (1988), 9 (3-4), 229-43, 1988, Abstract.
Han et al., "A New Side-Chain Anchoring Strategy for Solid-Phase Synthesis of Peptide Acids with C-Terminal Cysteine", Dept. of Chemistry, Univ. of Minnesota, pp. 385-388, 2001.
Cabrele et al., "Amino Acid Side Chain Attachment: A Convenient Strategy to Obtain C-Terminally Modified or Cyclic Peptides by Solid Phase Synthesis", Peptides, pp. 202-203 (1998).

(Continued)

*Primary Examiner*—Andrew D Kosar
*Assistant Examiner*—Satyanarayana R Gudibande
(74) *Attorney, Agent, or Firm*—Morgan, Lewis & Bockius LLP

(57) ABSTRACT

A process is provided for the solid-phase synthesis of a peptide amide which comprises attaching an α-nitrogen protected Cα-carboxamide amino acid to a solid support by its side chain, removing the α-nitrogen protecting group, assembling a peptide chain on said α-nitrogen and then cleaving the assembled peptide amide from the solid support. Novel amino acid analogues, peptide amides and solid-phase supports are also provided.

7 Claims, No Drawings

OTHER PUBLICATIONS

Solid-Phase Peptide Synthesis, Chapter 26, pp. 1291-1298, 1997.
"Synthesizing Peptides", www.appliedbiosystems.com, Aug. 5, 2001.

"Overview of Peptide Synthesis", www.anaspec.com, Aug. 5, 2001.
Ortigão, "The Chemistry of Peptide Synthesis", www.interativa.de chemistry of peptide synthesis, 2001.

* cited by examiner

PROCESS FOR THE SYNTHESIS OF PEPTIDES AMIDES BY SIDE-CHAIN ATTACHMENT TO A SOLID PHASE

BACKGROUND OF THE INVENTION

1. Field of the Invention

This invention relates to a process for the solid-phase synthesis of peptide amides, to Fmoc-α-nitrogen protected Cα-carboxamide amino acids, novel peptide amides and novel supports for peptide amide synthesis.

2. Description of Related Art

Many peptides have found utility as therapeutic agents. One peptide that is of particular importance is eptifibatide a cyclic peptide amide containing six amino acids and one mercaptopropionyl residue. Eptifibatide acts by binding to the platelet receptor glycoprotein IIb/IIIa and inhibiting platelet aggregation, thus preventing blood clots. Eptifibatide is the active agent in Integrelin™, which is used in treating patients with acute coronary syndrome and those undergoing percutaneous coronary intervention.

A solid-phase method for the production of eptifibatide is described in U.S. Pat. No. 5,318,899. However, as with many peptides the major challenge with eptifibatide is to produce sufficient material at an acceptable cost.

Peptides may be synthesised by solid-phase synthesis that commences from the carboxy-terminal end of the peptide using an alpha-amino protected amino acid. The two most widely used protocols employ tert-butyloxycarbonyl (Boc) or 9-fluorenylmethoxycarbonyl (Fmoc) as amino protecting groups.

When an Fmoc protection strategy is employed the favoured solid-phase support is a polydimethylacrylamide or polystyrene resin derivatised with a 4-(2',4'-dimethoxybenzyl-Fmoc-aminomethyl)-phenoxy (Fmoc-Rink amide) linkage agent. The first protected amino acid of the peptide sequence may be attached to this resin by converting its carboxyl group to an active ester, usually by reacting with N-hydroxybenzotriazole (BtOH) in the presence of an activating agent such as diisopropylcarbodiimide (DIC). This mild activation step minimises racemisation of susceptible residues such as Cys and Trp (throughout this specification standard three letter or single letter abbreviations for amino acids will be used). In addition, mild acidolysis of this peptide resin can result in both the cleavage of the peptide from the resin and the deprotection of any side chain protecting groups. However, the Fmoc-Rink amide linkage agent is an expensive reagent and this limits its use in commercial-scale peptide synthesis.

An alternative strategy is to use a resin bearing a 4-hydroxymethylbenzoic acid (HMBA) linkage unit. These derivatised resins are cheaper than those derivatised with the Fmoc-Rink amide linker. However, attachment of the first amino acid involves a p-dimethylaminopyridine (DMAP) catalysed esterification protocol that can result in both incidental Fmoc removal and racemisation of susceptible amino acids (Atherton, E. et al. (1981) J. Chem. Soc. Chem. Commun. p 336).

Peptides are usually converted to the corresponding amides by ammonolysis/aminolysis of resin bound peptide esters or by synthesis of the peptide amide using an amine based linker such as the Fmoc-Rink amide resin. Thus their production is also limited by the factors outlined above.

Therefore there is a requirement for a process by which peptide amides such as eptifibatide may be economically produced in high purity on a large scale.

BRIEF SUMMARY OF THE INVENTION

Thus, the present invention provides a process for the solid-phase synthesis of a peptide amide which comprises attaching an α-nitrogen protected Cα-carboxamide amino acid to a solid support via its side chain, removing the α-nitrogen protecting group and assembling a peptide chain on said α-nitrogen.

Preferably the assembled peptide amide is then cleaved from the solid support.

Preferably the α-nitrogen protected Cα-carboxamide amino acid comprises a heteroatom, such as N, O or S, in its side chain

DETAILED DESCRIPTION OF THE INVENTION

A preferred process for the solid-phase synthesis of a peptide amide which comprises the steps of:
  (a) attaching an α-nitrogen protected Cα-carboxamide amino acid comprising a heteroatom in its side chain to a solid support via said side chain;
  (b) deprotecting the α-nitrogen of the attached first amino acid by removing the α-nitrogen protecting group under conditions such that the attached first amino acid remains connected to the solid support and coupling an additional α-nitrogen protected amino acid to the unprotected α-nitrogen of the attached amino acid to yield an attached peptide amide with a protected N-terminus;
  (c) deprotecting the N-terminus of the attached peptide amide by removing the α-nitrogen protecting group under conditions such that the attached peptide amide remains connected to the solid support and coupling an additional α-nitrogen protected amino acid to the unprotected N-terminus of the attached peptide amide and repeating until the desired peptide amide is assembled on the solid support;
  (d) removing the α-nitrogen protecting group from the N-terminus of said peptide amide and optionally reacting with a non-amino acid N-terminal residue; and
  (e) cleaving the link between the side chain of the first Cα-carboxamide amino acid of the peptide amide and the solid support so that the peptide amide is released from the solid support and optionally removing any side chain protecting groups.

The peptide amide released in step (e) is preferably isolated and then purified.

The α-nitrogen protecting group is preferably a base labile protecting group. More preferably the α-nitrogen protecting group is Fmoc.

The α-nitrogen protected Cα-carboxamide amino acid may be derived from any amino acid with a side chain comprising a heteroatom. Preferably the sidechain comprises a nucleophilic moiety such as a nucleophilic N, O and S moiety. More preferably the α-nitrogen protected Cα-carboxamide amino acid is derived from Cys, Arg, Ser, Tyr, Thr, Lys, Om, Asp, Glu, Trp, His, Pen (penicillamine), Dpr (2,3-diaminopropionic Acid) and Dab (2,4-diaminobutyric acid). It is especially preferred that the α-nitrogen protected Cα-carboxamide amino acid is derived from Cys.

Based on the above preferences the most preferred α-nitrogen protected Cα-carboxamide amino acid is Fmoc-cysteine Cα-carboxamide (Fmoc-Cys-NH$_2$).

Nα-Fmoc Cα-carboxamide amino acids may be prepared by reacting the side chain of an amino acid with a protecting group and then amidating the Cα-carboxyl. Amidation is preferably carried out by converting the amino acid α-carboxyl group to an active ester followed by reaction with an amidating agent such as ammonium bromide/N-methylmorpholine. When a side chain protecting group is used it preferably comprises a trityl moiety. After amidation the trityl protecting group may be readily removed using known conditions such as by treating with, for example, trifluoroacetic acid and triisopropylsilane in a suitable solvent such as dichloromethane.

The solid support in step (a) may be any support known in the art that is suitable for use in solid-phase peptide synthesis. Such supports are able to react, commonly via a linking group, with a side chain of an amino acid, more preferably a nucleophilic amino acid side chain to form a bond which is stable during the acylation and deprotection cycles of steps (b), (c) and (d) yet allow release of the peptide amide in step (e).

Preferably the solid support is based on a polystyrene or polydimethylacrylamide polymer. More preferably the support is a copolymer of styrene with about 0.5 to 2% divinyl benzene as a cross-linking agent or a polydimethylacrylamide polymer comprising N,N-dimethylacrylamide, N,N-bisacryloylethylenediamine and acryloylsarcosine methyl ester monomers. Details of these preferred supports and other suitable supports may be found in Chan and White "Fmoc Solid-Phase Peptide Synthesis" Oxford University Press, 2000 which is incorporated herein by reference.

The preferred linker group comprises a trityl moiety, more preferably a 4-methoxytrityl moiety.

Based on the above preferences a particularly preferred solid support is 4-methoxytrityl polystyrene.

Step (a) may be carried out under the same conditions and in the same solvents as are commonly used in linking amino acids via their Cα-carboxyl to solid supports in peptide solid-phase synthesis. These methods are well known in the art and are described in many standard texts on the subject such as Atherton and Sheppard, "Solid-Phase Peptide Synthesis—A Practical Approach", IRL Press at Oxford University Press, 1989 and Chan and White "Fmoc Solid-Phase Peptide Synthesis" Oxford University Press, 2000, which are incorporated herein by reference.

When the resin is 4-methoxytrityl polystyrene and a Fmoc nitrogen protecting group is used, step (a) typically comprises dissolving the Nα-Fmoc Cα-carboxamide amino acid in a suitable solvent such as N,N-dimethylformamide then adding, with mixing, N,N-diisopropylethylamine. This Nα-Fmoc Cα-carboxamide amino acid solution is then added to the resin and allowed to react before collecting the resin and washing with a suitable solvent such as N,N-dimethylformamide.

The coupling and deprotection cycles of steps (b), (c) and (d) may be carried out using standard conditions for peptide solid-phase synthesis well known in the art. For further detail reference is made, for example, to Atherton and Sheppard, "Solid-Phase Peptide Synthesis—A Practical Approach", IRL Press at Oxford University Press, 1989 and Chan and White "Fmoc Solid-Phase Peptide Synthesis" Oxford University Press, 2000 which are incorporated herein by reference. When the protecting group used is Fmoc, it is particularly favoured that Fmoc removal is effected by treating with a solution of piperidine in N,N-dimethylformamide, more preferably 20% v/v piperidine in N,N-dimethylformamide.

Amino acid activation is preferably carried out in N,N-dimethylformamide in the presence of 1-hydroxybenzotriazole (BtOH) and diisopropylcarbodiimide.

In steps (b), (c) and (d) side chain protecting groups may be used to protect susceptible side chains which could otherwise be modified in the coupling and deprotection cycles. Examples of amino acids with susceptible side chains are Cys, Asp, Glu, Ser, Arg, Har, Tyr, Thr, Lys, Orn, Pen, Trp, Asn and Gin. Alternatively, a post solid-phase synthesis chemical modification of the peptide amide may be carried out to yield a desired side chain. For example following the process of U.S. Pat. No. 5,318,899 homoarginine can be prepared by guanidation of a lysine residue.

It has been found that in certain embodiments of a process according to the present invention that some side chain protecting groups may be omitted. Thus, in a preferred process of the present invention Fmoc-Arg and Fmoc-Har are coupled without the use of a side chain protecting group. This may be achieved by ensuring that post coupling of Arg or Har the guanidino group on the side chain of these amino acid residues is protonated prior to any further coupling reactions. This is preferably achieved by treating the resin bound peptide amide with an excess of BtOH.

The optional non-amino acid N-terminal residue in step (d) may be any compound able to react with the N-terminal of the peptide amide attached to the resin. Commonly, this compound is an organic acid, preferably a thiol substituted organic acid and more preferably a S-protected mercaptopropionic acid or a mercaptopropionic acid disulphide.

The precise conditions required to cleave the peptide amide from the solid support in step (e) vary with the nature of the side chain of the α-nitrogen protected Cα-carboxamide amino acid and the linker group on the support and are known in the art. Typically with the preferred combination of Cys and 4-methoxytrityl polystyrene the peptide amide may be released by treating the peptide amide resin with 10% (v/v) ethanedithiol in trifluoroacetic acid.

In step (e) any side chain protecting groups may be removed either before or after the link between the solid support has been cleaved. However, it is preferred that the link between the solid support and peptide amide and removal of any side chain protecting groups is carried out by a single process. It is also preferred that when step (d) does not involve reaction with a non-amino acid N-terminal residue that: the α-nitrogen protecting group is removed from the N-terminus, the link between the solid support and peptide amide and removal of any side chain protecting groups is carried out by a single process.

Isolation and purification of the peptide amide may be achieved using standard procedures and techniques that would be well known to one skilled in the art. These methods include precipitation of the peptide amide in a solvent that will not affect the integrity of the peptide amide, such as diisopropylether, followed by preparative HPLC, ion exchange chromatography and salt exchange.

The isolated peptide amide may be subjected to further processing, either before or after purification. Preferably the peptide amide following isolation and, optionally, purification is cyclised. More preferably the peptide amide is cyclised via the formation of a disulphide bridge between two residues in the peptide amide bearing available thiols.

Any suitable method may be used to cyclise the peptide amide via a disulphide bridge. Examples of methods known in the art are summarised by Albericio et al., in Chan and White "Fmoc Solid-Phase Peptide Synthesis" Oxford University Press, 2000, pages 91 to 114 which methods are incorporated herein by reference. Examples of such methods include: air oxidation; oxidation in the presence of redox buffers, such as Tris-buffer comprising EDTA and oxidised and reduced glutathione; dimethylsulphoxide (DMSO) mediated oxidation; potassium ferricyanide mediated oxidation; Ellman's reagent, 5,5'-dithiobis(2-nitrobenzoic acid) mediated oxidation; iodine mediated oxidation; thallium (III) trifluoroacetate mediated oxidation; alkyltrichlorosilane-sulphoxide mediated oxidation; silver trifluoromethanesulphonate-DMSO-aqueous HCl mediated oxidation; and directed disulphide formation using agents such as 2,2'-dithiobis(5-nitropyridine), 2,2'-dithiopyridine and bis(tert-butyl)azocarboxylate.

Preferably cyclisation is brought about by diluting the peptide amide which comprises two residues with available thiols in an aqueous medium to a concentration, for example less than 1 g per litre, which allows internal disulphide bond formation and then adjusting the pH to an alkaline pH such as from pH 7.5 to 10.5, preferably pH 8 to 10, more preferably pH 8.5 to 9.5 and especially around pH 9. It will be recognised that the optimum peptide concentration and pH will depend on a number of factors such as the nature of both the thiol and peptide.

Cyclisation may also be achieved by either:

(i) synthesising an analogue of the desired peptide amide with an additional thiol containing compound joined by a disulphide bridge to a thiol containing residue, preferably the N terminal residue, within the peptide amide. This additional thiol containing compound is preferably the same as the residue to which it is bound and is preferably cysteine, penicillamine or more preferably mercaptopropionic acid. This, disulphide-containing, peptide amide analogue is able to undergo an internal rearrangement reacting with a thiol on another residue in the peptide amide to yield a cyclic peptide amide; or (ii) synthesising a dimer of the desired peptide amide where the individual chains are linked by one or more disulphide bridges. These dimers are then under suitable conditions able to undergo internal rearrangement to yield either a single or two equivalents of the desired cyclic peptide.

The internal rearrangement in (i) and (ii) commonly involves diluting the peptide in an aqueous medium to a concentration, for example 5 to 20 g per litre, which allows internal disulphide bond formation and then adjusting the pH to an alkaline pH such as from pH 7.5 to 10.5, preferably pH 8 to 10, more preferably pH 8.5 to 9.5 and especially around pH 9. It will be recognised that the optimum peptide concentration and pH will depend on a number of factors such as the nature of both the thiol and peptide.

Preferably the peptide amide produced by the process comprises a Har-G-D grouping. More preferably the peptide amide produced by the process is able to form a disulphide-bridged cyclic compound. It is especially preferred that the peptide amide produced by this process is selected from the group consisting of:

```
HS-Mpr-A-Har-G-D-W-P-C-NH2

HS-Mpr-P-Har-G-D-W-P-C-NH2

HS-Mpr-G-Har-G-D-W-P-C-NH2

HS-Mpr-Aib-Har-G-D-W-P-C-NH2

HS-Mpr-(N-Me-Arg)-Har-G-D-W-P-C-NH2

HS-Mpr-(N-Me-Ser)-Har-G-D-W-P-C-NH2

HS-Mpr-(D-Ala)-Har-G-D-W-P-C-NH2

HS-Mpr-(B-Ala)-Har-G-D-W-P-C-NH2

HS-Mpr-(N-Me-Leu)-Har-G-D-W-P-C-NH2

HS-Mpr-(N-Me-Ala)-Har-G-D-W-P-C-NH2
```

-continued
```
HS-Mpr-Sar-Har-G-D-W-P-C-NH2

HS-Mpr-V-Har-G-D-W-P-C-NH2

HS-Mpr-Har-G-D-W-P-A-C-NH2

HS-Mpr-Har-G-D-W-P-(N-Me-Ala)-C-NH2

HS-Mpr-Har-G-D-W-P-C-NH2

HS-Mpr-Har-G-D-W-P-(D-Ala)-C-NH2

HS-Mpr-Har-G-D-W-P-P-C-NH2

HS-Mpr-Har-G-D-W-P-Sar-C-NH2

HS-Mpr-Har-G-D-W-P-Aib-C-NH2

HS-Mpr-A-Har-G-D-W-P-Pen-NH2

HS-Mpr-A-K-G-D-W-P-Pen-NH2

HS-Mpr-D-Har-G-D-W-P-Pen-NH2
```

Processes to produce peptide amides comprising dimers of any of the above compounds linked by a disulphide bridge or with an additional thiol compound linked by a disulphide bridge to a thiol in the peptide amide are also preferred.

It is especially preferred that the peptide amide produced by the process comprises the sequences:

```
HS-Mpr-Har-Gly-Asp-Trp-Pro-Cys-NH2;

Mpr-S-S-Mpr-Har-Gly-Asp-Trp-Pro-Cys-NH2;
or

-[S-Mpr-Har-Gly-Asp-Trp-Pro-Cys-NH2]2.
```

More especially it is preferred that the peptide amide produced by the process comprises the sequence HS-Mpr-Har-Gly-Asp-Trp-Pro-Cys-NH$_2$.

Preferably these linear peptide amides are then cyclised to give c[Mpr-Har-Gly-Asp-Trp-Pro-Cys]-NH$_2$ by means of a disulphide bridge between Cys and Mpr.

A preferred embodiment of the invention provides a process for the solid-phase synthesis of c[Mpr-Har-Gly-Asp-Trp-Pro-Cys]-NH$_2$ cyclised through a disulphide bridge between Cys and Mpr which comprises:
  (i) attaching the thiol side chain of Fmoc-Cys-NH$_2$ to an appropriate reactive solid support;
  (ii) carrying out a solid-phase peptide synthesis to form a linear peptide amide;
  (iii) cleaving the linear peptide amide from the solid support to yield a linear peptide amide of the sequence Mpr-S—S-Mpr-Har-Gly-Asp-Trp-Pro-Cys-NH$_2$, HS-Mpr-Har-Gly-Asp-Trp-Pro-Cys-NH$_2$ or -[S-Mpr-Har-Gly-Asp-Trp-Pro-Cys-NH$_2$]$_2$; and
  (iv) cyclising the peptide amide to form the product.

A more preferred embodiment of the invention provides a process for the solid-phase synthesis of c[Mpr-Har-Gly-Asp-Trp-Pro-Cys]-NH$_2$ cyclised through a disulphide bridge between Cys and Mpr which comprises:
  (i) attaching the thiol side chain of Fmoc-Cys-NH$_2$ to an appropriate reactive solid support;
  (ii) carrying out a solid-phase peptide synthesis without the use of a protecting group on the side chain of homoarginine to form a linear peptide;
  (iii) cleaving the linear peptide amide from the solid support to yield a linear peptide amide of the sequence HS-Mpr-Har-Gly-Asp-Trp-Pro-Cys-NH$_2$; and (iv) cyclising the peptide amide to form the product.

Preferred solid supports and process conditions are as defined above.

The processes of the present invention may use batch or continuous flow synthesis techniques or any automated synthesizer following the instructions provided by the manufacturer.

According to a second aspect of the invention there is provided an Fmoc-α-nitrogen protected Cα-carboxamide amino acid comprising a heteroatom in its side chain. More preferably the Fmoc-α-nitrogen protected Cα-carboxamide amino acid comprising a heteroatom in its side chain is selected from the group consisting of Fmoc-Cys-NH$_2$, Fmoc-Arg-NH$_2$, Fmoc-Ser-NH$_2$, Fmoc-Tyr-NH$_2$, Fmoc-Thr-NH$_2$, Fmoc-Lys-NH$_2$, Fmoc-Orn-NH$_2$, Fmoc-Asp-NH$_2$, Fmoc-Glu-NH$_2$, Fmoc-Trp-NH$_2$, Fmoc-His-NH$_2$, Fmoc-Pen-NH$_2$, Fmoc-Dab-NH$_2$, Fmoc-Dpr-NH$_2$.

Fmoc-α-nitrogen protected Cα-carboxamide amino acid comprising a heteroatom in its side chain may be prepared as described above in the first aspect of the invention.

A third aspect of the invention provides a disulphide dimer of a peptide amide comprising a Har-G-D grouping. It is preferred that compounds according to the third aspect of the invention are selected from the group consisting of:

```
-[S-Mpr-A-Har-G-D-W-P-C-NH2]2

-[S-Mpr-P-Har-G-D-W-P-C-NH2]2

-[S-Mpr-G-Har-G-D-W-P-C-NH2]2

-[S-Mpr-Aib-Har-G-D-W-P-C-NH2]2

-[S-Mpr-(N-Me-Arg)-Har-G-D-W-P-C-NH2]2

-[S-Mpr-(N-Me-Ser)-Har-G-D-W-P-C-NH2]2

-[S-Mpr-(D-Ala)-Har-G-D-W-P-C-NH2]2

-[S-Mpr-(B-Ala)-Har-G-D-W-P-C-NH2]2

-[S-Mpr-(N-Me-Leu)-Har-G-D-W-P-C-NH2]2

-[S-Mpr-(N-Me-Ala)-Har-G-D-W-P-C-NH2]2

-[S-Mpr-Sar-Har-G-D-W-P-C-NH2]2

-[S-Mpr-V-Har-G-D-W-P-C-NH2]2

-[S-Mpr-Har-G-D-W-P-A-C-NH2]2

-[S-Mpr-Har-G-D-W-P-(N-Me-Ala)-C-NH2]2

-[S-Mpr-Har-G-D-W-P-C-NH2]2

-[S-Mpr-Har-G-D-W-P-(D-Ala)-C-NH2]2

-[S-Mpr-Har-G-D-W-P-P-C-NH2]2

-[S-Mpr-Har-G-D-W-P-Sar-C-NH2]2

-[S-Mpr-Har-G-D-W-P-Aib-C-NH2]2

-[S-Mpr-A-Har-G-D-W-P-Pen-NH2]2

-[S-Mpr-A-K-G-D-W-P-Pen-NH2]2

-[S-Mpr-D-Har-G-D-W-P-Pen-NH2]2
```

A particularly preferred compound according to the third aspect of the invention has the sequence:

```
-[S-Mpr-Har-Gly-Asp-Trp-Pro-Cys-NH2]2.
```

A fourth aspect of the invention provides a peptide amide comprising a Har-G-D grouping comprising an additional thiol containing compound linked by a disulphide bond to a thiol in the peptide amide. It is preferred that the additional thiol containing compound is linked by a disulphide bond to the N-terminal thiol containing residue in the peptide. It is also preferred that the additional thiol containing compound is the same as the peptide residue to which it is linked by a disulphide bond. It is especially preferred that the additional thiol containing compound is mercaptopropionic acid and that it is linked to an N-terminal mercaptopropionic acid in a peptide amide.

It is preferred that compounds according to the fourth aspect of the invention are selected from the group consisting of:

```
Mpr-S-S-Mpr-A-Har-G-D-W-P-C-NH2

Mpr-S-S-Mpr-P-Har-G-D-W-P-C-NH2

Mpr-S-S-Mpr-G-Har-G-D-W-P-C-NH2

Mpr-S-S-Mpr-Aib-Har-G-D-W-P-C-NH2

Mpr-S-S-Mpr-(N-Me-Arg)-Har-G-D-W-P-C-NH2

Mpr-S-S-Mpr-(N-Me-Ser)-Har-G-D-W-P-C-NH2

Mpr-S-S-Mpr-(D-Ala)-Har-G-D-W-P-C-NH2

Mpr-S-S-Mpr-(B-Ala)-Har-G-D-W-P-C-NH2

Mpr-S-S-Mpr-(N-Me-Leu)-Har-G-D-W-P-C-NH2

Mpr-S-S-Mpr-(N-Me-Ala)-Har-G-D-W-P-C-NH2

Mpr-S-S-Mpr-Sar-Har-G-D-W-P-C-NH2

Mpr-S-S-Mpr-V-Har-G-D-W-P-C-NH2

Mpr-S-S-Mpr-Har-G-D-W-P-A-C-NH2

Mpr-S-S-Mpr-Har-G-D-W-P-(N-Me-Ala)-C-NH2

Mpr-S-S-Mpr-Har-G-D-W-P-C-NH2

Mpr-S-S-Mpr-Har-G-D-W-P-(D-Ala)-C-NH2

Mpr-S-S-Mpr-Har-G-D-W-P-P-C-NH2

Mpr-S-S-Mpr-Har-G-D-W-P-Sar-C-NH2

Mpr-S-S-Mpr-Har-G-D-W-P-Aib-C-NH2

Mpr-S-S-Mpr-A-Har-G-D-W-P-Pen-NH2

Mpr-S-S-Mpr-A-K-G-D-W-P-Pen-NH2

Mpr-S-S-Mpr-D-Har-G-D-W-P-Pen-NH2
```

A particularly preferred compound according to the fourth aspect of the invention has the sequence Mpr-S—S-Mpr-Har-Gly-Asp-Trp-Pro-Cys-NH$_2$ A fifth aspect of the invention provides a support for solid-phase synthesis which comprises a α-nitrogen protected Cα-carboxamide amino acid attached to the support through the side chain of the amino acid.

The support is as described in the first aspect of the invention and preferably is based on a polystyrene or polydimethylacrylamide polymer with a trityl linker.

Preferably the attached α-nitrogen protected Cα-carboxamide amino acid is derived from Cys, Arg, Ser, Tyr, Thr, Lys, Orn, Asp, Glu, Trp, His, Pen (penicillamine), Dpr (2,3-diaminopropionic Acid) and Dab (2,4-diaminobutyric acid). It is especially preferred that the α-nitrogen protected Cα-carboxamide amino acid is derived from Cys.

The α-nitrogen protecting group on the attached α-nitrogen protected Cα-carboxamide amino acid is preferably a base labile protecting group. More preferably the α-nitrogen protecting group is Fmoc.

Thus a preferred support according to the fifth aspect of the invention comprises a polystyrene or polydimethylacrylamide polymer with a trityl based linker to which a α-nitrogen protected Cα-carboxamide amino acid is attached by its side chain.

An especially preferred support comprises a polystyrene or polydimethylacrylamide polymer with a trityl linker to which a Fmoc-α-nitrogen-Cα-carboxamide amino acid is attached by its side chain wherein the amino acid is selected from the group consisting of Cys, Arg, Ser, Tyr, Thr, Lys, Orn, Asp, Glu, Trp, His, Pen, Dpr or Dab, especially Cys.

The invention is now illustrated but not limited by the following Examples.

EXAMPLE 1

Synthesis of Eptifibatide c[Mpr-Har-Gly-Asp-Trp-Pro-Cys]-NH$_2$

| Abbreviations | |
|---|---|
| DCM | Dichloromethane |
| DIC | Diisopropylcarbodiimide |
| DIPEA | N,N-Diisopropylethylamine |
| DMF | N,N-Dimethylformamide |
| EDT | 1,2-Ethanedithiol |
| Fmoc | 9-Fluorenylmethoxycarbonyl |
| Har | Homoarginine |
| BtOH | 1-Hydroxybenzotriazole |
| IPP | Diisopropylether |
| Mpr | 3-Mercaptopropionic acid |
| [Mpr-OH]$_2$ | 3-Mercaptopropionic acid disulphide |
| NMM | N-Methylmorpholine |
| TIPS | Triisopropylsilane |
| TFA | Trifluoroacetic acid |

Step 1 Fmoc-Cys-NH$_2$ Synthesis

Step 1 (a) Amidation of Fmoc-Cys(Trt)-OH

Fmoc-Cys(Trt)-OH (584.0 g) and BtOH.H$_2$O (306.0 g) were separately charged to a Duran flask and dissolved in DMF (6 litres). The flask was then immersed in an ice bath. Once the solution had reached <5° C. a single aliquot of DIC (155.8 ml) was added and the reaction mixture was stirred for 18 minutes to form the active ester. The flask was then removed from the ice bath, dried and allowed to warm to room temperature.

NH$_4$Br (107.7 g) was weighed into a dry Duran flask and DMF (800 ml) added with stirring until clear. An aliquot of NMM (120.8 ml) was then added with mixing to the solution of NH$_4$Br which was then charged to the activated Fmoc-amino acid solution. Over the first minute of mixing there was a distinct colour change from pale yellow to bright yellow. The reaction mixture was then stirred at room temperature for 4.5 to 18 hours.

The reaction mixture was transferred to a 5 litre round bottomed flask and evaporated in portions to approximately a third of the original volume (2.3 litres). The pale orange liquor was transferred to a 5 litre reaction flask and vigorously stirred with an overhead stirrer. Unreacted acidic BtOH was neutralised by the careful addition of 5% w/v NaHCO$_3$(aq.) (2.0 litres) and the resultant media diluted with H$_2$O (4.0 litres). During this stage the intermediate Fmoc-Cys(Trityl)-NH$_2$ precipitated as a dough-like white solid. This solid was filtered off, washed with water (3×4 litres) and air dried for 0.5 hours before being transferred to a desiccator and dried "in-vacuo" for 18 hours.

Step 1(b) Removal of the Trityl Protecting Group

The product of step 1(a), Fmoc-Cys(Trt)-NH$_2$ (585.0 g), was transferred to a 10 litre reactor vessel and dissolved in DCM (600 ml) over a 0.3 hour period using an overhead stirrer. An aliquot of TIPS (200 ml) was added to the reaction mixture, which was then immersed in an ice-bath prior to the addition of TFA (5.1 litres). The reaction mixture was stirred gently for 10 minutes at the reduced temperature and then allowed to return to room temperature and stirred for a further 1.5 hours. The reaction mixture was concentrated by evaporation to yield an oily solid. This product was reconstituted in DCM (1.0 litre) and evaporated once more to azeotope the TFA from the product. This resulted in a white solid which was extracted into ethyl acetate (3.0 litres) with vigorous stirring to yield a pale yellow solution. This solution was added to petroleum ether 60.80 (19.0 litres) with vigorous stirring to precipitate Fmoc-Cys-NH$_2$. Stirring was continued for 30 minutes to provide a homogeneous solid. This was filtered and washed 3 times with petroleum ether 60/80 (1.0 litre per wash). The resultant solid was then desiccated 'in-vacuo' for 18 hours. Precipitation by petroleum ether was repeated 3 times to remove any trityl-TIPS adduct from the product.

Step 2 Fmoc-Cys-NH$_2$ Attachment

Fmoc-Cys-NH$_2$ (745.1 g) from Step 1 was dissolved in DMF (2615 ml) with stirring. DIPEA (506 g) was then added to the resultant amino acid solution and mixed for one minute. This Fmoc-Cys-NH$_2$ solution was added to 4-methoxytrityl polystyrene resin (747 g) (from CBL-Patros, Greece) and the mixture was mixed for two hours then charged to a reactor vessel which allowed thereby removal of the solvent by filtration. The resin with Fmoc-Cys-NH$_2$ attached was then washed seven times with 9 L of DMF. The washed resin was then suspended in 10% v/v DIPEA in methanol (6.7 L) for 5 minutes before filtration and subsequent washing 7 times with 9 L of DMF.

Step 3 Fmoc-Group Removal

The Fmoc protecting group was removed by treating the resin from step 2 twice with 20% piperidine in DMF (2×9 L). In the first treatment the resin and piperidine/DMF mixture were agitated gently for 3 minutes before removing the piperidine/DMF by filtration. In the second treatment the resin and piperidine/DMF mixture were agitated gently for 7 minutes before removing the piperidine/DMF by filtration. The resin was then washed 7 times with DMF (7×9 L) removing the solvent by filtration.

Step 4 Amino Acid Activation and Addition

Fmoc-Pro-OH (661 g) and BtOH.H$_2$O (600 g) were dissolved in DMF (1949 ml) and cooled to less than 10° C. in an ice bath. DIC was added to the reaction mixture in 10 aliquots of 41 ml over 10 minutes with stirring. The temperature of the reaction mixture was monitored during the addition of DIC and kept below 20° C. The reaction mixture was agitated for a further 6 minutes and then added to the de-protected washed resin from Step 3. The coupling reaction was allowed to proceed for 6 hours at ambient temperature. Coupling efficiency was tested by the Kaiser test. The peptide amide-resin was then washed with DMF (9 L) and the protecting Fmoc-group removed as in Step 3.

The process described above was then repeated coupling Fmoc-Trp-OH (835 g) to the resin bound proline except that the chloranil test for secondatry amines was used in place of the Kaiser test.

Fmoc-Asp(OtBu)-OH (806 g) and Fmoc-Gly-OH (582 g) were coupled using the above protocol for Fmoc-Pro-OH.

Fmoc-Har-OH (894 g) was coupled using the same protocol as Fmoc-Pro-OH except that 900 g BtOH.H$_2$O was used. After the Har coupling and following the Fmoc-group removal and DMF washes (the volume of each wash being increased to 11.25 L) a solution of BtOH.H$_2$O (1125 g) in DMF (11.25 L) was added to the resin which was stirred for 5 minutes and then filtered.

[Mpr-OH]$_2$ (412 g) was coupled using the same protocol as for Fmoc-Pro-OH except that the volume of DMF used in the washes was increased from 9 L to 11.25 L.

The resin was collapsed prior to cleavage with DCM (5×7.50 L). The resin was then air dried for 1 hour.

Step 5 Peptide Amide Cleavage and Side Chain Protecting Group Removal

10% (v/v) EDT/TFA (15 litres) was mixed with the peptide amide resin from Step 4. A further aliquot of TFA (15 litres) was added while continuing to agitate. Thirty minutes after the initial charge the crude linear peptide amide solution was filtered from the resin. The resin was washed 3 times with TFA (3×15 litres). The combined filtrates were pooled and concentrated to an oil by rotary evaporation (bath temperature <35° C.). Evaporation was stopped when there was a sudden drop in the rate of evaporation. The resultant oil was gradually added to stirred IPP (100 litres). The evaporation flask was rinsed with TFA (2×250 ml) and these rinses were also added to the IPP with continued stirring. The mixture was agitated for a further 10 minutes and the resultant precipitated peptide amide left to settle out under gravity for a minimum of 30 minutes. The solid was filtered off and washed 3 times with IPP (3×20 litres) taking care not to draw excessive amounts of air through the material. The crude linear peptide amide was then dried overnight "in-vacuo" at 20° C. to constant weight.

Step 6 Peptide Amide Cyclisation

The peptide amide from Step 5 (200 g) was suspended in acetonitrile (1150 ml), and water (1150 ml) was added with mixing to provide a solution. This solution was then added to water (20.7 litres) with mixing. A solution of ammonia in water (3.5% w/v) was added to the peptide amide solution to adjust the pH to 9.0±0.25. The amount of ammonia required was approximately 2.0 ml/g crude peptide amide. If the pH exceeded pH 9.25 acetic acid was added to bring the pH value into the required range. The resultant solution was stirred until cyclisation was complete, monitoring by HPLC after four hours then at hourly intervals. The end point of the reaction was taken as when the amount of fully reduced linear peptide amide drops below 2.5%, as assessed by analytical HPLC.

The HPLC analysis method used to monitor the cyclisation was as follows:

| | |
|---|---|
| Buffer A | 6 mM HCl/water |
| Buffer B | Acetonitrile |
| Column | Waters SymmetryShield RP$_8$ 3.5 μm 100 Å 150 × 4.6 mm |
| Gradient | 10 to 35% Buffer B in Buffer A over 30 minutes |
| Flow rate | 1 cm$^3$/min |
| Wavelength | 204 nm |
| Injection volume | 10 μl |
| Temperature | 30° C. |
| Peak width | 1.0 |
| Peak sensitivity | 0.4 |

Step 7 Purification

Step 7(a) Preparative HPLC

The cyclised peptide amide solution from Step 6 was acidified with 10% citric acid in water (34 ml/g crude peptide amide) and stirred until it was dissolved. The resultant solution was filtered through a 0.45 μm filter and purified by preparative HPLC on Kromasil C8 (from Eka Nobel). The conditions were as follows:

| | |
|---|---|
| Media | Kromasil C8 (10μ, 100 Å, 3 kg) |
| Column dimensions | 25 × 15 cm internal diameter |
| Flow rate | 375 ml/min |
| Detection | 254 nm |
| Buffer A | 10 mM HCl/water |
| Buffer B | Acetonitrile |
| Gradient | 5% Buffer B in Buffer A for 10 minutes |
| | 5–30% Buffer B in Buffer A over 75 minutes |
| | 30–75% Buffer B in Buffer A over 5 minutes |

Peak fractions were collected, pooled and stored at 4° C. and further purified by salt exchange, desalting, evaporation and lyophilisation to yield the pure cyclic peptide amide.

EXAMPLE 2

Step 1

Step 1 was carried out as in Example 1, Step 1.

Step 2 Fmoc-Cys-NH$_7$ Attachment

Fmoc-Cys-NH$_2$ (418.5 g) from Step 1 was dissolved in DMF (2692 ml) with stirring. This was then transferred to a rotary evaporator and 25-50% of the DMF removed by evaporation (bath temperature <35° C.) The residual solution was made up to 3766 ml by the addition of further DMF. DIPEA (381 g) was then added to the resultant amino acid solution and mixed for one minute. This Fmoc-Cys-NH$_2$ solution was added to 4-methoxytrityl polystyrene resin (769 g) (from CBL-Patros, Greece) and the mixture was mixed for two hours then charged to a reactor vessel which allowed thereby removal of the solvent by filtration. The resin with Fmoc-Cys-NH$_2$ attached was then washed seven times with 9.23 L of DMF. The washed resin was then suspended in 10% v/v DIPEA in methanol (9.23 L) for 5 minutes before filtration and subsequent washing 7 times with 9.23 L of DMF.

Step 3 Fmoc-Group Removal

The Fmoc protecting group was removed by treating the resin from step 2 twice with 20% piperidine in DMF (2×9.23 L). In the first treatment the resin and piperidine/DMF mixture were agitated gently for 3 minutes before removing the piperidine/DMF by filtration. In the second treatment the resin and piperidine/DMF mixture were agitated gently for 7 minutes before removing the piperidine/DMF by filtration.

The resin was then washed 7 times with DMF (7×9.23 L) removing the solvent by filtration.

Step 4 Amino Acid Activation and Addition

Fmoc-Pro-OH (506 g) and BtOH.H$_2$O (405.3 g) were dissolved in DMF (2007 ml) and cooled to less than 5° C. in an ice bath. DIC was added to the reaction mixture in 10 aliquots of 31 ml over 10 minutes with stirring. The temperature of the reaction mixture was monitored during the addition of DIC and kept below 30° C. The reaction mixture was agitated for a further 6 minutes and then added to the de-protected washed resin from Step 3. The coupling reaction was allowed to proceed for 6 hours at ambient temperature. Coupling efficiency was tested by the Kaiser test. The peptide amide-resin was then washed with DMF (9.23 L) and the protecting Fmoc-group removed as in Step 3.

The process described above was then repeated coupling Fmoc-Trp-OH (639.7 g) to the resin bound proline except that the chloranil test for secondary amines was used in place of the Kaiser test.

Fmoc-Asp(OtBu)-OH (617.1 g) and Fmoc-Gly-OH (445.9 g) were coupled using the above protocol for Fmoc-Pro-OH.

Fmoc-Har.HCl—OH (744.9 g) was coupled using the same protocol as Fmoc-Pro-OH. After the Har coupling and following the Fmoc-group removal and DMF washes (the volume of each wash being increased to 11.53 L) a solution of BtOH.H$_2$O (1154 g) in DMF (10.35 L) was added to the resin which was stirred for 5 minutes and then filtered.

Trt-Mpr-OH (522.7 g) was coupled using the same protocol as for Fmoc-Pro-OH except that the volume of DMF used in the washes was increased from 9.23 L to 11.50 L.

The resin was collapsed prior to cleavage with DCM (5×7.69 L). The resin was then air dried for 1 hour.

Step 5 Peptide Amide Cleavage and Side Chain Protecting Group Removal

10% (v/v) EDT/TFA (15 litres) was mixed with the peptide amide resin from Step 4. A further aliquot of TFA (15 litres) was added while continuing to agitate. Thirty minutes after the initial charge the crude linear peptide amide solution was filtered from the resin. The resin was washed 3 times with TFA (3×5 litres). The combined filtrates were pooled and concentrated by rotary evaporation (bath temperature <35° C.). Evaporation was stopped when there were 5 litres remaining. The resultant solution was gradually added to stirred IPP (100 litres). The evaporation flask was rinsed with TFA (2×250 ml) and these rinses were also added to the IPP with continued stirring. The mixture was agitated for a further 10 minutes and the resultant precipitated peptide amide left to settle out under gravity for a minimum of 30 minutes. The solid was filtered off and washed 3 times with IPP (3×20 litres) taking care not to draw excessive amounts of air through the material. The crude linear peptide amide was then dried overnight "in-vacuo" at 20-25° C. to constant weight.

Step 6 Peptide Amide Cyclisation

The peptide amide from Step 5 (180 g) was suspended in acetonitrile (10.3 L), and water (10.3 L) was added with mixing to provide a solution. This solution was then added to water (186.2 litres) with mixing. A solution of ammonia in water (3.5% w/v) was added to the peptide amide solution to adjust the pH to 9.0±0.25. The amount of ammonia required was approximately 2.0 ml/g crude peptide amide. If the pH exceeded pH 9.25 acetic acid was added to bring the pH value into the required range. A solution of EDT in acetonitrile (1% v/v, 207 mls) was added to the peptide solution. The resultant solution was stirred until cyclisation was complete, monitoring by HPLC at 1-1.5 hour intervals. The end point of the reaction was taken as when the amount of fully reduced linear peptide amide drops below 2.5%, as assessed by analytical HPLC.

The HPLC analysis method used to monitor the cyclisation was as follows:

| | |
|---|---|
| Buffer A | 6 mM HCl/water |
| Buffer B | Acetonitrile |
| Column | Waters SymmetryShield RP$_8$ 3.5 μm 100 Å 150 × 4.6 mm |
| Gradient | 10 to 35% Buffer B in Buffer A over 30 minutes |
| Flow rate | 1 cm$^3$/min |
| Wavelength | 204 nm |
| Injection volume | 10 μl |
| Temperature | 30° C. |
| Peak width | 1.0 |
| Peak sensitivity | 0.4 |

The invention claimed is:

1. A process for the solid-phase synthesis of a peptide amide which comprises attaching Fmoc-cysteine Cα-carboxamide amino acid to a solid support, wherein the solid support is 4-methoxytrityl polystyrene via its side chain, removing the α-nitrogen protecting group and assembling a peptide chain on said α-nitrogen.

2. A process for the solid-phase synthesis of a peptide amide which comprises the steps of:
   (a) attaching Fmoc-cysteine Cα-carboxamide amino acid to a solid support, wherein the solid support is 4-methoxytrityl polystyrene via its side chain;
   (b) deprotecting the Fmoc-cysteine Cα-carboxamide amino acid by removing the Fmoc group under conditions such that the cysteine Cα-carboxamide amino acid remains connected to the solid support and coupling an additional α-nitrogen protected amino acid to the unprotected α-nitrogen of the cysteine Cα-carboxamide to yield an attached peptide amide with a protected N-terminus;
   (c) deprotecting the N-terminus of the attached peptide amide by removing the α-nitrogen protecting group under conditions such that the attached peptide amide remains connected to the solid support and coupling an additional α-nitrogen protected amino acid to the unprotected N-terminus of the attached peptide amide;
   (d) repeating step (c) until the desired peptide amide is assembled on the solid support;
   (e) removing the α-nitrogen protecting group from the N-terminus of said peptide amide and optionally reacting with a non-amino acid N-terminal residue; and
   (f) cleaving the link between the side chain of the cysteine Cα-carboxamide amino acid of the peptide amide and the solid support so that the peptide amide is released from the solid support and optionally removing any side chain protecting groups.

3. A process according to claim 2 comprising the additional steps:
   (g) isolating the peptide amide produced in stepf (f);
   (h) optionally purifying the isolated peptide from step (g); and
   (i) cyclising the peptide amide.

4. A process according to claim 3 wherein the peptide amide is cyclised via the formation of a disulphide bridge between two residues in the peptide amide.

5. A process according to either claim 1 or claim 2 for the solid-phase synthesis of c[Mpr-Har-Gly-Asp-Trp-Pro-Cys]-NH$_2$ cyclised through a disulphide bridge between Cys and Mpr which comprises:
  (i) attaching the thiol side chain of Fmoc-Cys-NH$_2$ to an appropriate reactive solid support;
  (ii) carrying out a solid-phase peptide synthesis to form a linear peptide amide;
  (iii) cleaving the linear peptide amide from the solid support to yield a linear peptide amide of the sequence Mpr-S—S-Mpr-Har-Gly-Asp-Trp-Pro-Cys-NH$_2$, HS-Mpr-Har-Gly-Asp-Trp-Pro-Cys-NH$_2$ or -[S-Mpr-Har-Gly-Asp-Trp-Pro-Cys-NH$_2$]2; and
  (iv) cyclising the peptide amide to form said c[Mpr-Har-Gly-Asp-Trp-Pro-Cys]-NH$_2$.

6. A process according to either claim 1 or claim 2 for the solid-phase synthesis of c[Mpr-Har-Gly-Asp-Trp-Pro-Cys]-NH$_2$ cyclised through a disulphide bridge between Cys and Mpr comprises:
  (i) attaching the thiol side chain of Fmoc-Cys-NH$_2$ to an appropriate reactive solid support;
  (ii) carrying out a solid-phase peptide synthesis without the use of a protecting group on the side chain of homoarginine to form a linear peptide amide;
  (iii) cleaving the linear peptide amide from the solid support to yield a linear peptide amide of the sequence H—S-Mpr-Har-Gly-Asp-Trp-Pro-Cys-NH$_2$; and
  (iv) cyclising the peptide amide to form said c[Mpr-Har-Gly-Asp-Trp-Pro-Cys]-NH$_2$.

7. A process according to claim 2 wherein c[Mpr-Har-Gly-Asp-Trp-Pro-Cys]-NH$_2$ is the peptide amide, 4-methoxytrityl polystyrene is the solid support and Fmoc is the c-nitrogen protecting group.

\* \* \* \* \*